United States Patent [19]

Frost

[11] Patent Number: 5,821,266

[45] Date of Patent: Oct. 13, 1998

[54] ANTIOXIDANT ACTIVITY OF 3-DEHYDROSHINKIMATES

[75] Inventor: John W. Frost, Okemos, Mich.

[73] Assignee: Michigan State University, East Lansing, Mich.

[21] Appl. No.: 684,452

[22] Filed: Jul. 19, 1996

[51] Int. Cl.⁶ .................................................. A61K 31/215
[52] U.S. Cl. .................... 514/529; 514/557; 523/455; 426/133; 426/654; 554/2; 252/407
[58] Field of Search ..................................... 514/529, 557; 523/455; 426/133, 654; 554/2; 252/407

[56] References Cited

U.S. PATENT DOCUMENTS 5,164,382  11/1992  Sutherland et al. ..................... 514/120
5,168,056  12/1992  Frost ..................................... 435/172.3
5,272,073  12/1993  Frost et al. ............................ 435/155

*Primary Examiner*—James H. Reamer
*Attorney, Agent, or Firm*—Marshall, O'Toole, Gerstein, Murray & Borun

[57] ABSTRACT

Dehydroshikimates are used as antioxidants for oxidation susceptible compositions, as well as for inhibiting oxidative physiological processes. Particularly, the parent acid and its derivatives find application in inhibiting the oxidation of food substances, feed, dietary supplements, oils, polymers, fuels, lubricants, cosmetics, medicinal agents, inks, dyes, and other oxidative sensitive products, over extended periods of time and at elevated temperatures. The subject compounds can be used at low concentrations.

19 Claims, 2 Drawing Sheets

ANTIOXIDANT ACTIVITY OF 3-DEHYDROSHINKIMATES

BACKGROUND

Oxidation is a ubiquitous process concerning almost all compounds exposed to air. Oxidation can be undesirable for a variety of purposes. In foods, oxidation can substantially deteriorate the organoleptic properties of a food particularly providing for offensive odors and tastes. In organic compounds, oxidation can deteriorate performance, change the characteristics of the composition, produce offensive products, and in some instances, be dangerous. For example, with lubricants, both lubricating oils and greases, oxidation results in substantial deterioration of the ability of the product to provide for lubrication and prevent wear. In many instances, the formation of the oxidized products can add to the wear of the equipment being lubricated. Plastics are subject to oxidative deterioration and for many applications must be stabilized using antioxidants. For cosmetics, oxidation can result in deterioration of the qualities of the product and impart undesirable characteristics. In the case of anesthetics, such as ether, oxidation can result in the production of peroxides which can have explosive effect. Even biological entities, such as humans and other vertebrates suffer from oxidative deterioration. Many of the naturally occurring substances present in mammals, such as tocopherol (Vitamin E), ascorbic acid (Vitamin C) and retinal (Vitamin A aldehyde) act to prevent oxidative deterioration of organs and tissues. There is, therefore substantial interest in being able to provide antioxidants which are effective at low concentrations.

The food industry uses large amounts of antioxidants. The most commonly employed antioxidants include BHA (a mixture of 2-t-butyl-4-methoxyphenol and 3-t-butyl-4-methoxyphenol), BHT (2,6-bis(1,1-dimethylethyl)-4-methylphenol), TBHQ (2-(1',1'-dimethylethyl)hydroquinone, n-propyl gallate, and vitamin E (α-tocopherol)). All of these antioxidants are available by chemical synthesis. Vitamin E, however, can also be obtained from deodorized corn or soybean oils, although the lower methylated tocopherols (beta, gamma, and delta) typically dominate the natural sourced tocopherol. The β-, γ-, and δ-tocopherols can be exhaustibly methylated to afford vitamin E, although this α-tocopherol carries a semi synthetic as opposed to natural label. Plant extracts derived from rosemary, sage, and grape seed constitute yet another class of naturally derived antioxidants.

There is a controversy surrounding the use of BHA, since at high doses, animals fed BHA have developed stomach cancer. This uncertainty surrounding BHA has fueled opposition to artificial antioxidants including BHT and TBHQ. Propyl gallate has not apparently been linked as an agent inducing cancer.

Dehydroshikimate is a known compound and is produced by a number of organisms, both naturally occurring and genetically modified. See, for example, U.S. Pat. Nos. 5,168,056 and 5,272,073, and references cited therein; Draths and Frost, *JACS* (1995) 117:2395–2400.

SUMMARY OF THE INVENTION

Dehydroshikimates, particularly the acid and its alkyl esters, find use as antioxidants in a wide variety of applications. Particularly, the dehydroshikimates find use as antioxidants in foods in low concentrations, where antioxidant activity is observed at elevated temperatures, or directly as an antioxidant to vertebrates. The dehydroshikimates are equal to or better than presently available antioxidants in a wide variety of applications.

Figure 1:
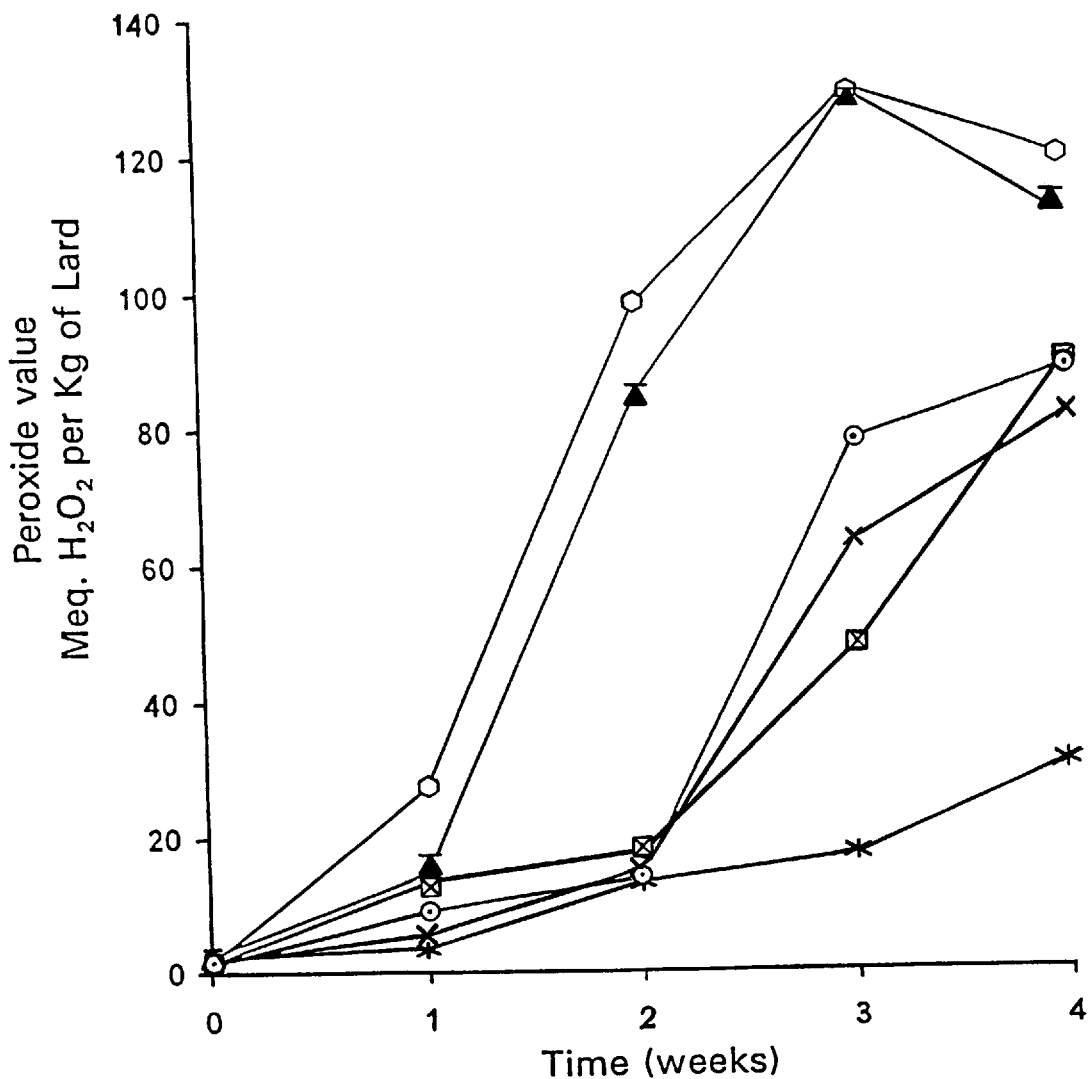
FIG. 1 is a graph describing the peroxide value of compounds according to this invention compared to commercially available products.

Solid circles=n-hexyl DHS; closed squares=n-propyl DHS; closed diamond=DHS; open circle=BHT; and open squares=mixed tocopherols.

DESCRIPTION OF THE SPECIFIC EMBODIMENTS

In accordance with the subject invention, compositions are provided having improved oxidative stability by the addition of a dehydroshikimate or for use as oxidation inhibitors in vertebrates. The compositions will generally have concentrations in the range of about 0.001 to 5 weight percent, usually in the range of about 0.005 to 1 weight percent, preferably in the range of about 0.01 to 0.05 weight percent, of the active oxidation inhibition portion of dehydroshikimate.

By dehydroshikimate is intended the core cyclic structure with at least the two hydroxy groups and the keto group bonded to annular carbon atoms and a carboxyl functionality at the 1-position. However, for some uses the carboxyl may be replaced with another functionality, particularly one which includes an atom having an unshared pair of electrons, such as oxygen in carbonyl, halogen, nitrogen in imino, amino, amidino, and the like. For the most part the carboxyl derivatives will be esters and amides. One or both of the hydroxyl groups may be derivatized, as esters or ethers of from 1 to 12, more usually 1 to 6, carbon atoms, particularly aliphatic, usually having from 0 to 1 site of unsaturation. Usually for the monoester of the annular hydroxyls, one will obtain a mixture of the two isomers, which may then be separated in accordance with conventional ways. Otherwise, the diester will be used.

The compounds of this invention will be at least 7 carbon atoms and not more than about 50 carbon atoms, usually not more than 30 carbon atoms, more usually not more than about 25 carbon atoms. Groups which may be used to derivatize the dehydroshikimate include methyl, ethyl, propyl, hexyl, octyl, dodecyl, acetyl, proprionyl, capryl, lauryl, stearyl, etc.

For administration to vertebrates, the dosage will usually be in the range of about 0.1 mg to 5 g or more, more usually in the range of about 1 mg to 1 g, where the dosage will depend on the purpose for the composition, frequency of administration, nature of the host, etc.

For the most part, the dehydroshikimates of this invention will have the following formula:

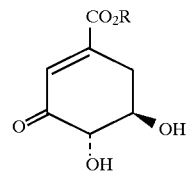

wherein R is hydrogen or alkyl of from 1–12, more usually from 2–10, preferably from 2–6 carbon atoms. The stereochemistry of the molecule may be naturally occurring or any of the stereoisomers, including racemic mixtures.

Any derivative may be used which provides the desired properties for its application, where the core antioxidant portion of the molecule is retained, while the carboxyl group may be modified to provide alternative functionalities, such as oxo, e.g. aldehyde and ketone or derivatives thereof, amino, thio, inorganic esters, e.g. phosphate, cyano, and the like. The active portion of the molecule may be joined to polymers, such as, polyvinyl alcohol or partially hydrolyzed polyvinyl acetate, acrylates and methacrylates, cellulose, or other appropriate backbone, e.g. physiologically acceptable backbone. For the most part, the monomeric molecule will be fewer than 50 carbon atoms, usually fewer than 30 carbon atoms. For use in foods, the derivative will be physiologically acceptable.

Dehydroshikimate acid can be obtained as indicated above by fermentation from a wide variety of organisms including Escherichia, Klebsiella, Aspergillus, as well as other bacteria and fungi. The esters may be readily prepared in accordance with conventional ways. Conveniently, the alkyl iodide, in the presence of a weakly basic catalyst, e.g. bicarbonate, may be combined with the dehydroshikimic acid under mild conditions in a polar organic solvent, e.g. DMF. The reaction may proceed for one or more days at room temperature with agitation. The product may then be extracted and purified.

Depending upon the particular composition being protected, varying amounts of the antioxidant may be employed within the ranges indicated above. The more severe the conditions, the more sensitive the product to oxidation, the longer the likely storage time, the higher the concentration which can be employed. In some instances, the amount may be determined empirically. In other situations, the maximum amount may be determined by the solubility or dispersibility of the antioxidant in the composition to be protected. The subject antioxidants may find use at elevated temperatures, being protective at temperatures of 200° C. or greater.

The products of this invention are processed products, in that they will have been subject to some modification by the hand of man, such as enrichment, purification, chemical modification, isolation, extraction, milling or other comminuting process, separation, and the like.

Of particular interest is the use of the subject compounds for foods for animal and human consumption. Foods may be fats, beverages, fresh foods, e.g. vegetables and fruits, grain derived foods, such as cereals, pasta, and the like, oils, baked goods, spices, and the like. Depending upon the nature of the product to be protected, the subject compositions may be mixed as an ingredient, sprayed on to the product, or any other convenient methodology may be used which provides for the appropriate distribution of the subject antioxidants to provide the desired protection. The particular manner of application is not essential to this invention, so long as the desired protection is achieved. The subject composition may be applied as a solution, powder, dispersion, or the like. The concentration may vary widely, depending upon the particular form in which the subject compositions are employed, varying from about 0.01 weight percent to 100 weight percent of the composition as employed.

The subject compositions may also find use in other applications, such as in lubricants, plastics, e.g. rubber or other elastomer, inks, dyes, oxygen sensitive organic molecules, e.g. ethers, drugs, vitamins, polyunsaturated organic compounds, etc. In those situations where elevated temperatures may be encountered, and the subject antioxidants become volatilized, the esters will have advantages over the acid in having a higher boiling point.

Plastics which will benefit from the use of the subject antioxidants include polyolefins, e.g. polyethylene, polypropylene, poly(4-methylpentene-1), polystyrene, etc., acrylates, polyformaldehyde, polyurethanes, polyamides, and the like. Because of their temperature stability, the subject compositions can be used during the molding and extrusion of various polymers to provide oxidation inhibition.

The subject compositions find use with fuels, lubricants and pressure transmission fluids, such as oils, greases, hydraulic fluids, and the like. Other applications include the use in cosmetics and oils, whether of plant, fossil fuel or animal origin, including during isolation, refining and storage.

The subject compositions may be used by themselves or in conjunction with other antioxidants, depending upon the composition to be protected. Since there are a diverse number of mechanisms which lead to oxidative degradation, different combinations of antioxidants may be advantageous with particular products to be protected. Other antioxidants which may be used in combination are those indicated previously as finding general use, as well as in combination with other antioxidants that scavenge free radicals (including, but not limited to Irganox 1010, Irganox 1076, ethoxyquin, and hindered amine light stabilizers), degrade peroxides and hydroperoxides by nonradical routes (thiodiproprionic acid and Irganox 1035), and deactivate metals towards redox reactions with peroxides by complexation and stabilization of the oxidized state of metal ions (citric acid, ethylenediaminetetraacetic acid, Irganox 1024 and inorganic phosphate.).

For use as a medicinal, the subject compositions can be formulated with other compositions, such as food, or may be formulated by themselves or in combination with other physiologically active compounds, such as vitamins, nutritional supplements, drugs, and the like. The subject compositions may be prepared as pills, powders, liquids, capsules, and the like. While for the most part, the subject compositions will be taken orally, they may also be taken parenterally, e.g. intravascularly, subcutaneously, etc. Other conventional components may be included as related to the nature of the formulation, such as flavoring, lubricant, antibiotic, etc.

The following examples are offered by way of illustration and not by way of limitation.

EXPERIMENTAL

Example 1. Preparation of 3-dehydroshikimate ("DHS").

Biocatalytic synthesis of DHS can be accomplished using any biocatalyst deficient in shikimate dehydrogenase activity. Shikimate dehydrogenase catalyzes the conversion of 3-dehydroshikimic acid into shikimic acid. The microbial biocatalyst should also express amplified levels of DAHP synthase and/or DAHP synthase insensitive to feedback inhibition by aromatic amino acids. DAHP synthase catalyzes the condensation of phosphoenolpyruvate with D-erythrose-4-phosphate which results in formation of 3-deoxy-D-arabino-heptulosonic acid 7-phosphate (DAHP). For an example of a DHS-synthesizing *E. coli* biocatalyst, see Draths, K. M., Frost, J. W. *J. Am. Chem. Soc.* 1990, 112, 9630.

DHS can be isolated from culture supernatants by acidification of the solution to pH 2.5 and extraction using refluxing ethyl acetate in a continuous liquid—liquid extractor where the aqueous solution is stirred. DHS can be obtained by subsequent removal of the ethyl acetate. Cooling of partially concentrated DHS-containing ethyl acetate solutions can be used to obtain crystalline DHS.

Example 2. Preparation of n-hexyl 3-dehydroshikimate.

To a suspension of DHS (1.5 g, 8.7 mmol) and $NaHCO_3$ (1.47 g, 17.4 mmol) in DMF (100 mL), a solution of n-hexyl iodide (5.2 mL, 34.9 mmol) in DMF (20 mL) was added at room temperature. After stirring the mixture for 5.5 days at room temperature, the solvent was removed and the residue extracted with ethyl acetate. The organic layer was washed with brine and dried over $MgSO_4$. Recrystallization from hexane/ethyl acetate afforded crystalline hexyl DHS (1.5 g, 67%): mp=88.5°–89.5° C.

Example 3. Preparation of n-propyl 3-dehydroshikimate.

To a suspension of DHS (1.5 g, 8.7 mmol) and $NaHCO_3$ (1.47 g, 17.4 mmol) in DMF (70 mL), a solution of n-propyl iodide (4.3 mL, 43.6 mmol) in DMF (30 mL) was added at room temperature. After stirring the mixture for two days at room temperature, the solvent was removed and extracted with ethyl acetate. The organic layer was washed with brine and dried over $MgSO_4$. recrystallization from hexane/ethyl acetate afforded crystalline propyl DHS (1.44 g, 80%): mp=99.5°–100.5° C.

Example 4. Antioxidant activity.

Peroxide formation, a characteristic of spoilage, was quantitated over the four week period by a standardized technique (A.O.C.S. Official Method Cd 8-53). The results are reported below and in FIG. 1

| Treatment | Storage time (week) | | | | |
|---|---|---|---|---|---|
| | 0 | 1 | 2 | 3 | 4 |
| control | 1.60 | 27.33 | 98.00 | 129.33 | 119.33 |
| +0.02% propyl gallate | 1.67 | 5.73 | 15.33 | 63.33 | 82.00 |
| +0.02% α-tocopherol | 2.60 | 14.67 | 84.67 | 128.66 | 110.67 |
| +0.02% DHS | 2.20 | 3.53 | 13.33 | 17.33 | 31.33 |
| +0.02% DHS-propyl ester | 1.47 | 13.33 | 18.00 | 48.00 | 90.00 |
| +0.02% DHS-hexyl ester | 1.07 | 9.05 | 14.00 | 78.00 | 88.67 |

Example 5. Antioxidant activity determined by an Oxidative Stability Instrument.

Figure 2:
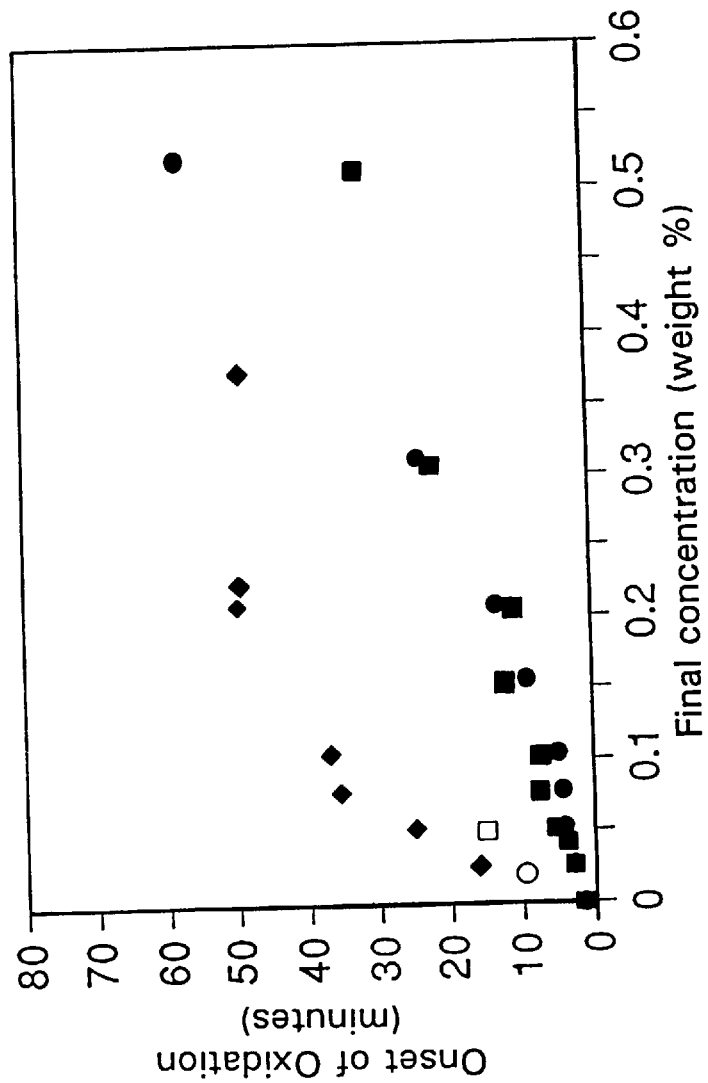
FIG. 2 is a graph of the results of an antioxidant test where the amount of volatiles produced at elevated temperatures is measured to determine the onset of oxidative decomposition for the subject compounds as compared to commercially available compounds.

OSI measurements were provided by an independent laboratory specializing in antioxidant spice extracts. DHS samples were dissolved in ethanol and the resulting solution added to lard. Both the hexyl DHS and propyl DHS dissolved in ethanol, but DHS did not completely dissolve in ethanol. Samples were heated at 110° C. in the presence of air. Volatiles resulting from oxidation of the lard are measured by the OSI which automatically records the length of time before onset of oxidative decomposition. The longer the length of time before onset of decomposition, the better the antioxidant characteristics of the antioxidant being tested. Onset of oxidative decomposition came at 1.2–1.6 minutes for the control run, consisting of a lard sample lacking antioxidants. The results are reported in FIG. 2.

It is evident from the above result that DHS results in lower formation of peroxide than either α-tocopherol and propyl gallate at the concentration of 0.02% which was employed. In addition, DHS is shown to be a better antioxidant than comparable weight percents of BHT and mixed tocopherols in the OSI test, where the esters are found almost as effective as the parent acid.

It is evident from the above results that the subject compositions provide effective protection from oxidation under severe conditions. The subject compositions can be employed at elevated temperatures, so that they can be used in a wide range of situations with greatly varying severity, where mechanisms of oxidation and oxidative degradation of the protected product may vary. The subject compositions can be readily prepared in good yield and in pure form, so they may find use not only in products which are not ingested, but also in products which are ingested.

The subject compounds can also be provided in sufficiently pure form to be used as an antioxidant, by themselves, or in conjunction with drugs to inhibit physiological processes associated with oxidation, such as nascent oxygen, ozonides, superoxide, peroxides, and the like.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A processed product subject to oxidative degradation comprising in an amount sufficient to inhibit such oxidation a 3-dehydroshikimate or derivative thereof.

2. A product according to claim 1, wherein said derivative is an alkyl ester of from 1–12 carbon atoms.

3. A product according to claim 1, wherein said product is a food or drug and said derivative is physiologically acceptable.

4. A product according to claim 1, wherein said product is a plastic.

5. A product according to claim 1, wherein said product is a lubricant.

6. A product susceptible to oxidation comprising from 0.001–5 weight percent of 3-dehydroshikimic acid or derivative thereof.

7. A product according to claim 6, wherein said derivative is an alkyl ester of from 1–12 carbon atoms.

8. A product according to claim 7, wherein said ester is the propyl ester.

9. A product according to claim 7, wherein said ester is the hexyl ester.

10. A product according to claim 6, wherein said 3-dehydroshikimic acid or derivative is the acid.

11. In a method for protecting a composition from oxidative degradation, by combining said composition with an oxidative inhibiting amount of an antioxidant, the improvement which comprises:

using a 3-dehydroshikimate as the antioxidant.

12. A method according to claim 11, wherein said composition is a food and said 3-dehydroshikimate is physiologically acceptable.

13. A method according to claim 11, wherein said composition is a plastic.

14. A method according to claim 11, wherein said composition is a lubricant.

15. A method according to claim 11, wherein said derivative is an alkyl ester of from 1–12 carbon atoms.

16. A method according to claim 15, wherein said ester is the propyl ester.

17. A method according to claim 15, wherein said ester is the hexyl ester.

18. A method according to claim 11, wherein said 3-dehydroshikimate is the acid.

19. A method according to claim 11, wherein said 3-dehydroshikimate is present in from 0.001–5 weight percent.

* * * * *